United States Patent [19]

Ritter et al.

[11] Patent Number: 4,900,544
[45] Date of Patent: Feb. 13, 1990

[54] CATIONIC POLYMERS AS ANTISTATIC ADDITIVES FOR HAIR PREPARATIONS

[75] Inventors: Wolfgang Ritter, Hilden; Rolf Tenhaef, Dusseldorf; Horst Hoffkes, Dusseldorf-Hellerhof; Kurt Seidel, Dusseldorf, all of Fed. Rep. of Germany

[73] Assignee: Henkel Kommanditgesellschaft auf Aktien, Duesseldorf, Fed. Rep. of Germany

[21] Appl. No.: 883,024

[22] Filed: Jul. 8, 1986

Related U.S. Application Data

[60] Continuation of Ser. No. 665,253, Oct. 26, 1984, abandoned, which is a division of Ser. No. 525,972, Aug. 24, 1983, abandoned.

[30] Foreign Application Priority Data

Feb. 21, 1983 [DE] Fed. Rep. of Germany ....... 3305964

[51] Int. Cl.$^4$ ............................................. A61K 7/075
[52] U.S. Cl. .................................... 424/70; 514/880; 514/881
[58] Field of Search .................... 424/70, 78; 514/880, 514/881

[56] References Cited

U.S. PATENT DOCUMENTS 3,626,029  12/1971  Young ................................. 525/232

FOREIGN PATENT DOCUMENTS 958644   12/1974  Canada .
1022075  6/1977   Canada .
1021264  11/1977  Canada .
1342269  3/1974   United Kingdom .
2067196  7/1981   United Kingdom .
1602560  11/1981  United Kingdom .

OTHER PUBLICATIONS

Lunn et al., "The Electrostatic Properties of Human Hair," J. Soc. Cosmetic Chem. 28 pp. 549–569, 1977.
Torrey, *Health Care Products Recent Developments*, pp. 192–217, 1981.

Primary Examiner—John W. Rollins
Assistant Examiner—W. Catchpole
Attorney, Agent, or Firm—Ernest G. Szoke; Wayne C. Jaeschke; Norvell E. Wisdom, Jr.

[57] ABSTRACT

An aqueous hair-treatment preparation containing an antistatic additive imparting an antistatic effect to the hair, characterized in that said antistatic additive is at least one cationic polymer produced by the process of (1) epoxidizing 1,3-diene homopolymers or copolymers (2) reacting the epoxide compound so produced with low molecular weight amines selected from the group consisting of primary amines, secondary amines and tertiary amines, and (3) converting the reaction products into the salt form or into polymeric quaternary ammonium salts. The use of these polymeric amine salts or quaternary ammonium salts in cosmetic hair-treatment preparations provides these preparations with antistatic effects. Preferred cationic polymers are obtained by the epoxidation of polybutadiene, of which more than 50% of the monomer units show the 1,4-cis-configuration, reaction with dimethylamine or morpholine and conversion into the hydrochlorides or alkylation with glycidyl trimethylammonium chloride, 3-chloro-2-hydroxypropyl trimethylammonium chloride or ethylene oxide. The cationic polymers are preferably used in shampoos in quantities of from 0.5 to 5.0% by weight in addition to 5 to 30% by weight of alkylether sulfate tensides and 1 to 5% by weight of a zwitterionic or amphoteric washing-active substance.

19 Claims, No Drawings

CATIONIC POLYMERS AS ANTISTATIC ADDITIVES FOR HAIR PREPARATIONS

This application is a continuation of application Ser. No. 665,253, filed Oct. 26, 1984, now abandoned, which is a division of Ser. No. 525,972, filed Aug. 24, 1983, now abandoned.

BACKGROUND OF THE INVENTION

1. Field of the Invention

This invention relates to cosmetic hair-treatment preparations containing an antistatic additive imparting an antistatic effect to the hair.

After washing with shampoos, shower and bath preparations based on synthetic tensides, but above all after cosmetic treatments, such as dyeing and shaping, hair is often in a cosmetically unsatisfactory state. It is difficult to comb when wet and has little hold and body after drying. Above all, it tends to become statically charged which causes freshly washed hair to "fly".

It is known that conditioning preparations can be applied to hair after washing, dyeing or permanent waving. Conditioning preparations generally contain cationic interface-active compounds as their active ingredients. It is also known that certain substances may be added to normal shampoos based on anion-active tensides or on mixtures of tensides of different ionogenity in order to obtain a certain conditioning effect when the hair is washed. Examples of substances of the type in question are water-soluble proteins or protein degradation products, polycationic polymers, such as for example the synthetic polymers containing quaternary ammonium groups described in German published patent application No. 21 09 081 (and equivalent Canadian Pat. No. 958,644) or the cellulose ethers containing quaternary nitrogen which are known from German published patent application No. 24 23 833 (and equivalent Canadian Pat. No. 1,022,075).

However, known conditioning agents have considerable drawbacks. Although cationic tensides are highly effective in nonionic formulations, they can only be used in ineffective quantities, if at all, in shampoos or, for example, hair dyes containing anionic tensides on account of their limited compatibility with anionic tensides. In addition, anionic tenside complex with quaternary ammonium compounds make the hair very "heavy", which is reflected in a greasy appearance and lack of body of the treated hair.

This "heaviness" is also observed to a greater or lesser extent in the case of known, cation-active formulations for the after treatment of hair.

Although polycationic polymers bring about a satisfactory improvement in wet compatibility, they do not effectively reduce the tendency of dry hair towards static charging. In many cases, particularly in anionic or anionic-amphoteric shampoo formulations, cationic polymers can even lead to an increase in the static chargeability of dry hair.

2. Objects of the Invention

An object of the invention is to obtain a cosmetic hair-treatment preparation containing an antistatic additive imparting an antistatic effect to the hair.

Another object of the invention is the development of an aqueous hair-treatment preparation containing an antistatic additive imparting an antistatic effect to the hair, characterized in that said antistatic additive is at least one cationic polymer obtainable by the process comprising (1) epoxidizing 1,3-diene homopolymer or copolymers containing at least 10 1,3-diene units to a conversion of at least 10% of the double bonds present, (2) reacting the epoxidized poly-1,3-dienes with amines having the formula $R^1NR^2R^3$, in which $R^1$ is a member selected from the group consisting of hydrogen, lower alkyl containing from 1 to 4 carbon atoms and hydroxyalkyl containing from 2 to 4 carbon atoms, and $R^2$ and $R^3$ are members selected from the group consisting of hydrogen, lower alkyl containing from 1 to 4 carbon atoms, and hydroxyalkyl containing from 2 to 4 carbon atoms, and together with the nitrogen atom, morpholino, piperidino and piperazino, with the proviso that at least one of $R^1$, $R^2$ and $R^3$ is other than hydrogen, (3) converting the reaction products with mineral acids or lower molecular weight carboxylic acids into the salt form, preferably into the hydrochlorides, or converting the polymeric tertiary amines into quaternary ammonium salts by alkylation with compounds selected from the group consisting of 3-chloro-2-hydroxypropyl trimethylammonium chloride, RCl, RBr, $R_2SO_4$, in which R represents methyl or ethyl or by the addition of ethylene oxide, propylene oxide, glycidol or glycidyl trimethylammonium chloride and conversion into the salt form, preferably into the hydrochlorides.

A further object of the present invention is the development of an aqueous hair-treatment composition comprising at least one hair-treatment agent and an additive to impart an antistatic effect to the hair, wherein said hair-treatment composition contains an amount sufficient to impart an antistatic effect to the hair of at least one cationic polymer produced by the process comprising (1) epoxidizing an unsaturated polymer selected from the group consisting of 1,3-diene homopolymers and copolymers from 1,3-diene monomers, said unsaturated polymer containing at least 10 1,3-diene units up to a conversion of at least 10% of the double bonds present, (2) reacting the epoxidized unsaturated polymer with amines having the formula $R^1NR^2R^3$, in which $R^1$ is a member selected from the group consisting of hydrogen, lower alkyl group containing from 1 to 4 carbon atoms and hydroxy-alkyl containing 2 to 4 carbon atoms and $R^2$ and $R^3$ are members selected from the group consisting of hydrogen, lower alkyl containing from 1 to 4 carbon atoms, hydroxyalkyl containing from 2 to 4 carbon atoms and together with the nitrogen atom, morpholino, piperidino and piperazino, with the provisio that at least one of $R^1$, $R^2$ and $R^3$ is other than hydrogen, (3) converting the aminated polymer to the salt form by a process selected from the group consisting of (a) acidifying with an acid selected from the group consisting of mineral acids and low-molecular-weight carboxylic acids having from 1 to 7 carbon atoms, (b) quaternizing the tertiary aminated polymer by reaction with a quaternizing compound selected from the group consisting of 3-chloro-2-hydroxypropyl trimethyl ammonium chloride, RCl, RBr and $R_2SO_4$, wherein R is member selected from the group consisting of methyl and ethyl and (c) quaternizing the tertiary aminated polymer by reaction with a quaternizing compound selected from the group consisting of ethylene oxide, propylene oxide, glycidol and glycidyl trimethyl ammonium chloride followed by acidifying with said acid of (a) above.

A yet further object of the present invention is the development of a process for imparting an antistatic effect to hair which comprises applying to hair the above aqueous hair-treatment composition.

These and other objects of the invention will become more apparent as the description thereof proceeds.

DESCRIPTION OF THE INVENTION

Accordingly, there was a need to find conditioning agents which are suitable for use as conditioning and antistatically active additives for hair treatment preparations and which are attended by the above-mentioned disadvantages to a far lesser extent, if at all.

The present invention relates to the use of cationic polymers obtainable by (1) epoxidizing 1,3-diene homopolymer or copolymers containing at least 10 1,3-diene units to a conversion of at least 10% of the double bonds present, (2) reacting the epoxidized poly-1,3-dienes with amines having the formula $R^1NR^2R^3$, in which $R^1$ is a member selected from the group consisting of hydrogen, lower alkyl containing from 1 to 4 carbon atoms and hydroxyalkyl containing from 2 to 4 carbon atoms, and $R^2$ and $R^3$ are members selected from the group consisting of hydrogen, lower alkyl containing from 1 to 4 carbon atoms, and hydroxyalkyl containing from 2 to 4 carbon atoms, and together with the nitrogen atom, morpholino, piperidino and piperazino, with the proviso that at least one of $R^1$, $R^2$ and $R^3$ is other than hydrogen, (3) converting the reaction products with mineral acids or lower molecular weight carboxylic acids into the salt form, preferably into the hydrochlorides, or converting the polymeric tertiary amines into quaternary ammonium salts by alkylation with compounds selected from the group consisting of 3-chloro-2-hydroxypropyl trimethyl ammonium chloride, RCl, RBr, $R_2SO_4$, in which R is methyl or ethyl, or by the addition of ethylene oxide, propylene oxide, glycidol or glycidyl trimethyl ammonium chloride and conversion into the salt form, preferably into the hydrochlorides, as an antistatically active additive in cosmetic hair-treatment preparations.

More particularly, the present invention relates to an aqueous hair-treatment composition comprising at least one hair-treatment agent and an additive to impart an antistatic effect to the hair, wherein said hair-treatment composition contains an amount sufficient to impart an antistatic effect to the hair of at least one cationic polymer produced by the process comprising (1) epoxidizing an unsaturated polymer selected from the group consisting of 1,3-diene homopolymer and copolymers from 1,3-diene monomers, said unsaturated polymer containing at least 10 1,3-diene units, to a conversion of at least 10% of the double bonds present, (2) reacting the epoxidized unsaturated polymer with amines having the formula $R^1NR^2R^3$, in which $R^1$ is a member selected from the group consisting of hydrogen, lower alkyl containing from 1 to 4 carbon atoms and hydroxyalkyl containing from 2 to 4 carbon atoms and $R^2$ and $R^3$ are members selected from the group consisting of hydrogen, lower alkyl containing from 1 to 4 carbon atoms, hydroxyalkyl containing from 2 to 4 carbon atoms and, together with the nitrogen atom, morpholino, piperidino and piperazino, with the provisio that at least one of $R^1$, $R^2$ and $R^3$ is other than hydroxygen, (3) converting the aminated polymer to the salt form by a process selected from the group consisting of (a) acidifying with an acid selected from the group consisting of mineral acids and low-molecular-weight carboxylic acids having from 1 to 7 carbon atoms, (b) quaternizing the tertiary aminated polymer by reaction with a quaternizing compound selected from the group consisting of 3-chloro-2-hydroxypropyl trimethyl ammonium chloride, RCl, RBr and $R_2SO_4$, wherein R is a member selected from the group consisting of methyl and ethyl, and (c) quaternizing the tertiary aminated polymer by reaction with a quaternizing compound selected from the group consisting of ethylene oxide, propylene oxide, glycidol and glycidyl trimethyl ammonium chloride followed by acidifying with said acid of (a) above; as well as a process for imparting an antistatic effect to hair which comprises applying to hair the above aqueous hair-treatment composition.

The cationic polymers suitable for use in accordance with the invention and the processes by which they are produced are known.

Thus, the epoxidation of butadiene oligomers is described, for example, in Chemiker-Zeitung 95 (1971), No. 20, pages 857 to 863. The reaction of epoxidized polybutadienes with tertiary amines to form quaternary ammonium polymers is known from published German patent application Ser. No. 21 41 941 (and corresponding British publication 1,342,269). The reaction of epoxidized butadiene homopolymers or copolymers with primary and secondary aliphatic and cycloaliphatic amines is described in published German patent application Ser. No. 27 32 736 (and corresponding British publication 1,602,560). Conversion of the polymeric tertiary amines, which are formed during the reaction of the polyepoxides with secondary amines, into polymeric quaternary ammonium salts may also be carried out in known manner by alkylation with 3-chloro-2-hydroxypropyl trimethylammonium chloride, methyl chloride, ethyl chloride, dimethyl sulfate, diethyl sulfate or by the addition of 1,2-monoepoxides, such as ethylene oxide, propylene oxide, glycidol or glycidyl trimethylammonium chloride.

Suitable starting products for producing the cationic polymers used in accordance with the invention are 1,3-diene homopolymers or copolymers. Suitable 1,3-dienes are, above all, butadiene, 1,3-pentadiene, isoprene and chloroprene. Liquid butadiene homopolymers or copolymers are preferably used. However, mono-olefins, such as ethylene, propylene, styrene, or acrylic acid derivatives may also be present as comonomers. The poly-1,3-dienes should contain at least 10 1,3-diene units per molecule. Liquid butadiene homopolymers are particularly suitable. The double bonds present in poly-1,3-dienes of the type in question may have the cis-configuration or trans-configuration or may be arranged in the vinyl position, depending on the polymerization conditions. It is preferred to use polymers of which more than 50% show the 1,4-cis-configuration at the double bonds.

The poly-1,3-dienes should be epoxidized up to a conversion of at least 10% of the double bond present. Polyepoxides containing from 3 to 6% by weight of epoxide oxygen are particularly suitable.

Amines suitable for reaction with the polyepoxides are, for example, methylamine, ethylamine, isopropylamine, monoethanolamine, dimethylamine, diethylamine, diethanolamine, morpholine, piperidine, piperazine, trimethylamine, triethylamine, triethanolamine, N,N-dimethylethanolamine. The reaction products with dimethylamine and morpholine are preferred.

The reaction with tertiary amines leads directly to polymeric quaternary ammonium compounds which are converted into the salt form by reaction with mineral acids or with low molecular weight carboxylic acids, preferably having from 1 to 7 carbon atoms, such as acetic acid, lactic acid, glycolic acid. Conversion with hydrochloric acid into the hydrochlorides is preferred.

The reaction with primary and secondary amines leads to polymeric secondary and tertiary amines which, after conversion into the salt form, are suitable as cationic polymers for use in accordance with the invention.

However, the polymeric tertiary amines obtained by reaction with secondary amines may also be converted by alkylation into polymeric quaternary ammonium compounds. It is preferred to convert reaction products of epoxidized poly-1,3-dienes with dimethylamine into polymeric quaternary ammonium salts by alkylation with glycidyl trimethylammonium chloride or with 3-chloro-2-hydroxypropyl trimethylammonium chloride. Another preferred group of cationic polymers for use in accordance with the invention is obtained by reacting the poly-1,3-diene epoxides with dimethylamine and quaternizing the reaction products obtained by the addition of ethylene oxide, followed by conversion into the salt form.

The use of the cationic polymers obtainable as described in accordance with the invention in cosmetic hair treatment preparations provides these preparations with a distinct antistatic effect when applied to human hair without any of the increased "heaviness" which normally occurs with cation-active compounds. By virtue of this effect, cosmetic hair-treatment preparations of the type in question considerably improve the set and body of the hair. This effect is surprising insofar as known cationic polymers produce hardly any antistatic effects, particularly when applied from formulations containing anionic tensides.

Antistatic activity may be tested, for example, as follows:

Strands of hair approximately 20 cm long and weighing approximately 2 g are subjected to a single bleaching treatment and to a single cold-wave treatment using standard commercial preparations (without the cationic polymers used in accordance with the invention), washed, rinsed and dried. 0.5 ml of a test solution containing, for example, 1% by weight of the cationic polymer is applied by pipette to the strands of hair thus pretreated and rubbed in. Instead of using the test solution, it is also possible to use any cosmetic hair-treatment preparation containing the cationic polymers to be used in accordance with the invention. After the treatment, the strands of hair are rinsed with clear, warm (35° C.) water, dried for 30 minutes at 60° C. and then conditioned for 24 hours at 20° C./50% relative air humidity.

Thereafter, the strands of hair are combed 20 times using a hard rubber comb. In the case of the untreated hair samples, this produces considerable static charging of the strands of hair, as reflected in a distinct spreading of the hair ends.

The strands of hair treated with the cationic polymers used in accordance with the invention or with preparations containing them are not statically charged and remain parallel after combing.

Cosmetic hair-treatment preparations suitable for use in accordance with the invention are, for example, shampoos, hair after treatment preparations, for example hair rinses, hair cure preparations, hair lotions, hair lacquers, hair sprays, hair dyes and hair waving preparations. However, the products may also be used with advantage in bath additives, shower baths and liquid body shampoos because they are also used for washing the hair or come into contact with the hair in use.

The cationic polymers used in accordance with the invention are incorporated in the cosmetic hair-treatment preparations mentioned above in quantities of from 0.1% to 10% by weight and preferably in quantities of from 0.5% to 5.0% by weight, based on the preparation as a whole or in the case of aerosol preparations, on the propellent-free active solution.

The cationic polymers used in accordance with the invention are particularly effective in cosmetic hair-treatment preparations containing anionic surface-active compounds, because an antistatic effect would otherwise be impossible to obtain with preparations such as these. Suitable anionic surface-active compounds are, for example, alkali metal, magnesium, ammonium and/or lower alkanol ammonium salts of alkyl sulfuric acid half esters containing from 8 to 18 and preferably from 12 to 16 carbon atoms in the alkyl (so-called alkyl sulfates) or of alkyl polyethyleneglycol ether sulfuric acid half esters containing from 8 to 18 and preferably from 12 to 16 carbon atoms in the alkyl and from 1 to 6 ethyleneglycol ether groups in the molecule (so-called alkyl ether sulfates). Other suitable anionic surface-active compounds are primary and secondary, linear alkane sulfonates containing from 10 to 18 carbon atoms, alkene sulfonates containing from 10 to 18 carbon atoms and hydroxy alkane sulfonates containing from 10 to 18 carbon atoms, of the type obtained by sulfonating linear olefins containing from 10 to 18 carbon atoms, higher fatty acid alkylol amide sulfates and higher fatty acid alkylol amide polyethyleneglycol ether sulfates, sulfated higher fatty acid monoglycerides, sulfosuccinic acid monoalkyl esters containing from 8 to 18 carbon atoms in the alkyl or dialkyl esters containing from 6 to 10 carbon atoms in the alkyls, alkyl polyethyleneglycol ether carboxylates containing from 8 to 18 carbon atoms in the alkyl and from 2 to 6 polyethyleneglycol ether groups in the molecule, acyl sarcosines, acyl taurides and acyl isethionates containing from 8 to 18 carbon atoms in the acyl groups.

In addition to the anionic surface-active compounds, zwitterionic or amphoteric wash-active substances may be used in quantities of up to about half the content of anionic surface-active compounds. Suitable zwitterionic wash-active substances are, for example, alkyl betaines, alkyl aminopropyl betaines, alkyl imidazolinium betaines, alkyl amidocarboxylic acids, in each case containing from 8 to 18 carbon atoms in the alkyl. Examples of such suitable zwitter-ionic tensides are cocoalkyl dimethylaminoacetic acid, cocoalkylamidopropyl dimethylaminoacetic acid or N-hydroxyethyl-N-cocoalkylamidoethyl glycine.

The cationic polymers are preferably used in accordance with the invention in a shampoo which, in addition to 0.5 to 5% by weight of the cationic polymer, contains from 5 to 30% by weight of alkylether sulfate tensides and from 1 to 5% by weight of a zwitterionic or amphoteric wash-active substance.

In addition, refatting constituents, such as for example ethoxylated higher fatty acid partial glycerides or glycerol polyethyleneglycol ether higher fatty acid esters, ethoxylated sorbitan higher fatty acid esters and also cosmetic oil components may be used in addition to the above-mentioned components.

The cosmetic hair-treatment preparations may also contain non-ionic wash active substances and the usual additives and auxiliaries, active substances, solvents, propellent gases, thickeners, dyes, opacifiers, fragrances, preservatives, stabilizers and buffers appropriate to the particular application or formulation.

The following Examples are intended to illustrate the invention without limiting it in any way.

EXAMPLES (A) Preparation of the Cationic Polymers

Example 1: Epoxidation of polybutadiene

In a glass apparatus consisting of a 4-liter three-necked flask, stirrer and intensive condenser, 540 g of a polybutadiene of which the viscosity at 20° C. according to DIN 53015 amounted to approximately 3 poises and the iodine number (according to Wijs) amounted to approximately 450 g/100 g and which predominantly contained 1,4-cis-double bonds (Polyöl hüls 130, a product of Chem. Werke Huls A. G., Germany were dissolved in 2000 ml of chloroform. 190 g of 40% peracetic acid (in glacial acetic acid) containing 19 g of dissolved sodium acetate were added dropwise over a period of 7.5 hours with vigorous stirring to the solution previously heated to 50° C. in such a way as to produce a steady, gentle reflux of the chloroform boiling under the effect of the heat of reaction. Thereafter, the reaction mixture was stirred for another 2 hours at 50° C. and then cooled to 30° C. The epoxide was precipitated by pouring the reaction mixture into 12,000 ml of methanol under continuous stirring. The viscous oil, precipitating to the bottom of the container, was separated off, mixed three times with 5 liters of methanol and separated and then washed until neutral. The oily reaction product was freed from volatile constituents in vacuo. The yield amounted to 95% of the theoretical. The product contained 2.5% by weight of epoxide oxygen.

Examples 2 to 8

Starting with 540 g of polybutadiene, epoxidation was carried out in the same way as in Example 1 using the quantities of peracetic acid (40% in glacial acetic acid) shown in Table 1. The yields and epoxide oxygen contents indicated were obtained.

TABLE 1

| Example No. | Quantity of peracetic acid (40% in glacial acetic acid) | Yield [% of the theoretical] | % Epoxide oxygen [% by weight] |
|---|---|---|---|
|   | 190 g | 95 | 2.5 |
| 2 | 285 g | 93 | 3.6 |
| 3 | 380 g | 88.5 | 4.7 |
| 4 | 570 g | 83.7 | 6.7 |
| 5 | 665 g | 64.3 | 7.4 |
| 6 | 950 g | 79.0 | 9.3 |
| 7 | 1140 g | 71.1 | 10.3 |
| 8 | 1425 g | 47.5 | 5.8 |

Example 9

Reaction of the epoxidized polybutadienes with dimethylamine 50 g of a 40% aqueous solution of dimethylamine were added to 50 g of epoxidized polybutadiene (Example 1) dissolved in 600 g of dioxane and the combined solutions introduced into an autoclave of V4A-steel. After purging twice with nitrogen, the contents of the autoclave were stirred under an initial pressure of 5 bars and at the same time heated to 200° C., producing a maximum pressure of 32 bars. After cooling to 20° C., the autoclave was vented and opened and the reaction product precipitated by pouring into 2.5 liters of distilled water. The isolated reaction product was purified by dissolution in dioxane and precipitation in water and, after drying, was characterized by the amine number. The reaction product had an amine number of 55.3. The yield amounted to 60% of the theoretical.

Examples 10 to 16

The reaction of the epoxidized polybutadienes (Examples 2 to 8) was carried out in the same way as in Example 9 starting with 50 g of the epoxides in 600 ml of dioxane, the amines shown in Table 2 being used. Reaction products having the amine numbers indicated in Table 2 were obtained.

TABLE 2

| Example No. | Epoxide used | Amine used Type | Quantity | Reaction product amine number |
|---|---|---|---|---|
| 9 | Example 1 | dimethylamine* | 50 g | 55.3 |
| 10 | Example 2 | dimethylamine* | 70 g | 69.1 |
| 11 | Example 5 | dimethylamine* | 90 g | 134.8 |
| 12 | Example 5 | monoethanolamine | 61 g | 98.5 |
| 13 | Example 6 | dimethylamine* | 120 g | 107.8 |
| 14 | Example 6 | methylamine* | 225 g | 240.4 |
| 15 | Example 8 | dimethylamine* | 105 g | 168.2 |
| 16 | Example 8 | morpholine | 81 g | 153.8 |

*40% aqueous solution

Examples 10a to 16a

Preparation of the hydrochlorides

The amine reaction products of Examples 9 to 16 were dissolved in dioxane and an equivalent quantity of 18% aqueous hydrochloric acid calculated from the amine number was added to the resulting solutions. The solvent was then removed by evaporation in vacuo.

Example 17

Quaternization with glycidyl trimethylammonium chloride 10 g of the amine reaction product of Example 9 was dissolved in 100 ml of dioxane, followed by the addition of 50 mg of KOH and mixing with 1.8 g of glycidyl trimethylammonium chloride (80%, moist). The reaction mixture was heated under reflux to boiling point over a period of 2 hours and kept at that temperature for another 5 hours, during which it became slightly cloudy. The reaction mixture was then concentrated to a volume of 50 ml and precipitated by pouring into 250 ml of distilled water. The substance precipitated was separated off and dried. The yield amounted to 9.7 g (i.e. 82.2% of the theoretical).

Conversion into the hydrochloride was carried out as in Examples 9 to 16.

Examples 18 and 19

The amine reaction products indicated in Table 3 were alkylated as in Example 17 with the indicated quantities of glycidyl trimethylammonium chloride (GMAC) and the yields of the hydrochloride obtained are indicated.

TABLE 3

| Example No. | Amine reaction product | GMAC, 80% | Yield % of theoretical | $Cl^{(-)}$ (% by weight) |
|---|---|---|---|---|
| 17 | Example 9 | 1.8 g | 82.2 | 0.48 |
| 18 | Example 10 | 2.2 g | 72.9 | 2.18 |
| 19 | Example 11 | 4.4 g | 55.6 | 0.36 |

Example 20

Quaternization with ethylene oxide 20 g of the reaction product of Example 10 were dissolved in 400 ml of anhydrous dioxane and 0.5 g of sodium methylate added to the resulting solution. The solution was then transferred to an autoclave, followed by the addition of 5.4 g of ethylene oxide (i.e. approximately 5 mols/mol of amino groups). After heating to 70° C. the solution was stirred for 5 hours at that temperature. In that time, the pressure which was initially 5 bars fell to 4.1 bars. After cooling, the reaction mixture was concentrated to dryness under reduced pressure. An addition of approximately 1 mol of ethylene oxide per amino group is calculated from the yield of 21.1 g obtained.

The quaternization product was converted into the readily water-soluble hydrochloride by dissolution in dioxane followed by the addition of approximately 5 g of 18% hydrochloric acid and concentration to dryness.

(B) Application Examples

Example 21

| Hair Shampoo | | |
|---|---|---|
| Fatty alcohol ($C_{12-18}$) + 2 EO-sulfate, Na salt (28%) | 30% | by weight |
| Cocoalkylamidopropyl betaine (30%) | 15% | by weight |
| Cationic polymer of Example 10 (hydrochloride) | 2.0% | by weight |
| Formaldehyde (40%) | 0.2% | by weight |
| Water, perfume oil, dyes | ad 100% | by weight |

EO = mols of ethylene oxide

Example 22

| Hair rinse | | |
|---|---|---|
| Cetyl alcohol "Lorol" C16, a product of E.I. DuPont Corp., U.S.A. | 1.5% | by weight |
| Glycerol mono-/distearate "Cutina" GMS, a product of Henkel KGaA, F.R. Germany | 1.5% | by weight |
| Cationic polymer of Example 16 (hydrochloride) | 1.5% | by weight |
| Cetyl trimethylammonium chloride (25%) | 2.0% | by weight |
| Water, perfume oil, dye | ad 100% | by weight |

Example 23

| Hair dye (brown) | |
|---|---|
| Tallow fatty alcohol | 8.0% by weight |
| Fatty alcohol ($C_{12-18}$) + 2 EO-sulfate, Na salt (28%) | 25.0% by weight |
| Cationic polymer of Example 18 | 3.0% by weight |
| p-tolylene diamine | 1.5% by weight |
| 2,4 diaminoanisole | 0.04% by weight |
| p-aminophenol | 0.23% by weight |
| Resorcinol | 0.4% by weight |
| Ammonia, 25% | 4.5% by weight |
| Water | ad 100% by weight |

The preceeding specific embodiments are illustrative of the practice of the invention. It is to be understood however that other expedients known to those skilled in the art or disclosed herein, may be employed without departing from the spirit of the invention or the scope of the appended claims.

We claim:

1. An aqueous shampoo composition for human hair consisting essentially of:
   (A) anionic surfactant present in an anionic surfactant effective amount;
   (B) amphoteric or zwitterionic surfactant present in an amphoteric or zwitterionic surfactant effective amount; and
   (C) cationic antistatic agent present in an antistatic effective amount, which agent is a cationic polymer that is the reaction product from:
      (1) a 1,3-diene homopolymer or predominantly 1,3-diene copolymer, having at least 10 1,3-diene units per molecule, in which at least 10% of the double bonds present have been epoxidized and which contains about 3–6% by weight of epoxide oxygen and which has been aminated with
      (2) amine selected from the group consisting of morpholine, piperidine, piperazine, and amines of the formula $R^1NR^2R^3$, wherein $R^1$ is a $C_{1-4}$ alkyl or a $C_{2-4}$ hydroxyalkyl; and $R^2$ and $R^3$ are the same or different and are each hydrogen, a $C_{1-4}$ alkyl, or a $C_{2-4}$ hydroxyalkyl; and then converted to a salt by
      (3)

11

(a) reacting the aminated epoxidized 1,3-diene polymer with a $C_{1-7}$ carboxylic acid or a mineral acid; or (b) alkylating the aminated epoxidized 1,3-diene polymer with 3-chloro-2-hydroxypropyl trimethylammonium chloride, RCl, RBr, or $R_2SO_4$ wherein R is methyl or ethyl, to form a quaternary ammonium salt; or (c) quaternizing the aminated epoxidized 1,3-diene polymer with ethylene oxide, propylene oxide, glycidol, or glycidyl trimethylammonium chloride; and then further reacting the resulting product with a $C_{1-7}$ carboxylic acid or a mineral acid.

2. The shampoo composition of claim 1 wherein said 1,3-diene homopolymer or predominantly 1,3-diene copolymer is a homopolymer of 1,3-butadiene, 1,3-pentadiene, isoprene, or chloroprene or a copolymer of 1,3-butadiene, 1,3-pentadiene, isoprene, or chloroprene with ethylene, propylene, styrene, or acrylic acid derivatives.

3. The shampoo composition of claim 2 wherein more than 50% of the double bonds of said polymer are in a 1,4-cis-configuration.

4. The shampoo composition of claim 2 wherein said 1,3-diene is a butadiene homopolymer or copolymer which is liquid under ambient conditions.

5. The shampoo composition of claim 4 wherein said 1,3-diene is a butadiene homopolymer whose viscosity at 20° C. according to DIN 53,015 is approximately 3 poises.

6. The shampoo composition of claim 1 wherein epoxidation of said 1,3-diene polymer is by reaction with peracetic acid.

7. The shampoo composition of claim 1 wherein said amine is selected from the group consisting of methylamine, ethylamine, isopropylamine, monoethanolamine, dimethylamine, diethylamine, diethanolamine, morpholine, piperidine, piperazine, trimethylamine, triethylamine, triethanolamine, and N,N-dimethylethanolamine.

8. The shampoo composition of claim 7 where said amine is dimethylamine, monoethanolamine, methylamine or morpholine.

9. The shampoo composition of claim 1, wherein item (a) or (c) of part (3) is selected and said acid is acetic acid, lactic acid, glycolic acid, or hydrochloric acid.

10. The shampoo composition of claim 9 wherein item (3) (c) is selected and quaternization is with ethylene oxide.

11. The shampoo composition of claim 2, wherein:

(1) said amine is selected from the group consisting of methylamine, ethylamine, isopropylamine, monoethanolamine, dimethylamine, diethylamine, diethanolamine, morpholine, piperidine, piperazine, trimethylamine, triethylamine, triethanolamine, and N,N-dimethylethanolamine; and (2) in item (a) or (c) of part (3), said acid is acetic acid, lactic acid, glycolic acid, or hydrochloric acid.

12. The shampoo composition of claim 1 wherein:

(1) said 1,3-diene polymer is a butadiene homopolymer which is liquid under ambient conditions and

12 wherein more than 50% of the double bonds of said polymer are in a 1-4-cis-configuration;

(2) said amine is dimethylamine, monoethanolamine, methylamine, or morpholine; and (3) in item (3) (a) or (c) said acid is hydrochloric acid; in item (3) (b), the alkylating agent is 3-chloro-2-hydroxypropyl trimethyl ammonium chloride; and in item (3) (c) the quaternizing agent is glycidyl trimethylammonium chloride.

13. The shampoo composition of claim 1 wherein said anionic surfactant is:

(i) an alkali metal, magnesium, ammonium, or $C_{1-7}$-alkanol salt of a $C_{8-18}$-alkyl sulfuric acid half ester;

(ii) a $C_{8-18}$-alkyl poly (1–6) ethylene glycol ether sulfuric acid half ester;

(iii) a primary or secondary linear $C_{10-18}$-alkane sulfonate;

(iv) a $C_{10-18}$-alkene sulfonate;

(v) a hydroxy $C_{10-18}$-alkane sulfonate;

(vi) a higher fatty acid alkylol amide sulfate;

(vii) a higher fatty acid aklylol amide polyethylene glycol ether sulfate;

(viii) a sulfated higher fatty acid monoglyceride;

(ix) a sulfosuccinic acid $C_{8-18}$-monoalkyl ester;

(x) a sulfosuccinic acid $C_{6-10}$-dialkyl ester;

(xi) a $C_{8-18}$-alkyl poly (2–6) ethyleneglycol ether carboxylate;

(xii) a $C_{8-18}$-acyl sarcosine;

(xiii) a $C_{8-18}$-acyl tauride;

(xiv) a $C_{8-18}$-acyl isethionate; or (xv) a mixture thereof or salt thereof.

14. The shampoo composition of claim 1 wherein said amphoteric or zwitterionic surfactant is:

(i) a $C_{8-18}$-alkyl betaine;

(ii) a $C_{8-18}$-alkyl aminopropyl betaine;

(iii) a $C_{-18}$-alkyl imidazolinium betaine;

(iv) a $C_{8-18}$alkyl amidocarboxylic acid; or (v) a mixture thereof or salt thereof.

15. The shampoo composition of claim 13 wherein said amphoteric or zwitterionic surfactant is:

(i) a $C_{8-18}$-alkyl betaine;

(ii) a $C_{8-18}$-alkyl aminopropyl betaine;

(iii) a $C_{-18}$-alkyl imidazolinium betaine;

(iv) a $C_{8-18}$-alkyl amidocarboxylic acid; or (v) a mixture thereof or salt thereof.

16. The shampoo composition of claim 14 wherein said anionic surfactant is a $C_{8-18}$-alkyl poly (1–6) ethyleneglycol ether sulfuric acid half ester.

17. The shampoo composition of claim 13 wherein said amphoteric or zwitterionic surfactant is: cocoalkyl dimethylaminoacetic acid; cocoalkylamidopropyl dimethylaminoacetic acid; or N-hydroxyethyl-N-cocoalkylamidoethyl glycine.

18. The shampoo composition of claim 16 wherein said anionic surfactant is present in about 5–30% by weight, said amphoteric or zwitterionic surfactant is present in about 1–5% by weight, and said cationic antistatic agent is present in about 0.1–10% by weight, all based upon the total weight of said composition.

19. The shampoo composition of claim 18 wherein said cationic antistatic agent is present in about 0.5–5% by weight.

* * * * *